United States Patent
Sartor et al.

(10) Patent No.: US 8,703,800 B2
(45) Date of Patent: Apr. 22, 2014

(54) NITRATE AND DIAZENIUMDIOLATE DERIVATIVES OF PIOGLITAZONE

(75) Inventors: Dirk Sartor, Rimbach (DE); Armin Scherhag, Dornach (CH)

(73) Assignee: Cardiolynx AG, Basel (CH)

( * ) Notice: Subject to any disclaimer, the term of this patent is extended or adjusted under 35 U.S.C. 154(b) by 0 days.

(21) Appl. No.: 13/701,100

(22) PCT Filed: Jun. 1, 2011

(86) PCT No.: PCT/EP2011/059015
§ 371 (c)(1),
(2), (4) Date: Nov. 30, 2012

(87) PCT Pub. No.: WO2011/151362
PCT Pub. Date: Dec. 8, 2011

(65) Prior Publication Data
US 2013/0072525 A1 Mar. 21, 2013

(30) Foreign Application Priority Data
Jun. 2, 2010 (EP) .................................. 10164771

(51) Int. Cl.
*A61K 31/44* (2006.01)
*C07D 417/00* (2006.01)

(52) U.S. Cl.
USPC ...................................... 514/341; 546/269.7

(58) Field of Classification Search
USPC ........................................ 514/341; 546/269.7
See application file for complete search history.

(56) References Cited

U.S. PATENT DOCUMENTS 5,585,495 A * 12/1996 Huber ........................... 548/183
2011/0230520 A1 9/2011 Sartor et al.

FOREIGN PATENT DOCUMENTS

WO 02/30867 4/2002
WO 2004/004648 1/2004

OTHER PUBLICATIONS

International Search Report issued Sep. 22, 2011 in International (PCT) Application No. PCT/EP2011/059015.
Dirk Sartor et al., U.S. Appl. No. 13/641,747, entitled "Valsartan Derivatives Carrying Nitrogen Oxide Donors for the Treatment of Vascular and Metabolic Diseases", filed Oct. 17, 2012.
Dirk Sartor et al., U.S. Appl. No. 13/131,722, entitled "Nitrate Derivatives of Cilostazol for the Treatment of Vascular and Metabolic Diseases", filed May 27, 2011.

* cited by examiner

*Primary Examiner* — Rei-tsang Shiao
(74) *Attorney, Agent, or Firm* — Wenderoth, Lind & Ponack, L.L.P.

(57) ABSTRACT

Nitrate ester and diazeniumdiolate derivatives of pioglitazone are described. They have valuable properties in the treatment of vascular and metabolic diseases, for example type 2 diabetes.

9 Claims, 2 Drawing Sheets

NITRATE AND DIAZENIUMDIOLATE DERIVATIVES OF PIOGLITAZONE

FIELD OF THE INVENTION

The invention relates to nitrate ester and diazeniumdiolate derivatives of pioglitazone useful in the treatment of type 2 diabetes.

BACKGROUND OF THE INVENTION

Vascular and metabolic diseases are, despite cancer, the leading causes of death in the Western World. Although many different ways of treating vascular and metabolic diseases are known, there is still a need for improved medication. Lifestyle modifications and drug therapy can decrease and delay the morbidity and mortality associated with these diseases. Diabetes of type 1 is successfully treated with insulin, while insulin treatment is only partially effective in diabetes of type 2. The type 2 diabetes is the most frequent one, particularly in elderly people.

One class of compounds promising in the treatment of type 2 diabetes are compounds derived from thiazolidinedione, so called glitazones. They are sensitizing tissue to insulin, thereby allowing the endogenous insulin to more efficiently lower the glucose level in the bloodstream. Examples of marketed glitazones are rosiglitazone and pioglitazone.

Pioglitazone selectively stimulates the nuclear receptor peroxisome proliferator-activated receptor gamma (PPAR-γ) and to a lesser extent PPAR-α. Via modulation of the transcription of the insulin-sensitive genes involved in the control of glucose and lipid metabolism in the muscle, adipose tissue and the liver, pioglitazone reduces insulin resistance in peripheral tissues and the liver resulting ultimately in reduced plasma levels of glucose, insulin and glycosylated haemoglobin (HbA1c). By its effects on lipid metabolism, pioglitazone also decreases the level of triglycerides and increases that of high-density lipoproteins (HDL) without changing low-density lipoproteins (LDL) and total cholesterol in patients lipid disorders.

Pioglitazone is indicated for the oral treatment of diabetes mellitus type 2 (previously known as non-insulin-dependent diabetes mellitus, NIDDM) as monotherapy and in combination with a sulfonylurea, metformin or insulin to optimize glucose control. The treatment effects of pioglitazone on glucose levels (efficacy) are, like with other treatments indicated for type 2 diabetes, best reflected by monitoring its effects on lowering HbA1c levels, which are considered to be reflective for the long-term efficacy of any blood glucose lowering agent.

However, the effectiveness of pioglitazone is not considered sufficient and might be improved without increasing the respective doses of pioglitazone by enhancing its effects on muscular metabolism with novel, thiazolidinedione-based compounds which exhibit additional properties over pioglitazone. Compared to increasing the doses of pioglitazone in case of unsatisfactory effectiveness, such novel compounds may also have a more favourable adverse event profile compared to increasing doses of pioglitazone for the typical side effects such as fluid retention and peripheral oedema. Muscular metabolism can be increased, e.g., by physical activity (exercise) which increases both, glucose utilization by the muscular tissue and muscular insulin sensitivity. Similar effects can, however, also be achieved by increasing perfusion of muscular tissue by increasing peripheral perfusion in the microvasculature and thus more efficient glucose dispersal in the sceletal muscles.

Donation of NO is the typical pharmacological effect of organic nitrates and specifically nitrate esters, such as glyceryl trinitrate (nitroglycerine), isosorbide dinitrate, or pentaerythrityl tetranitrate, which act all as coronary vasodilators and improve symptoms and exercise tolerance in patients with coronary artery disease due to atherosclerosis, who are suffering from angina pectoris and one of the established standard treatments. Most organic nitrates (e.g. mononitrates and trinitrates) are fast acting pharmaceuticals with a relatively short halflife and have the typical disadvantage that patients develop a nitrate tolerance, meaning that part of the pharmacodynamic effect is lost during chronic treatment and a three times daily dosing regimen.

Nitrate esters of drugs in general are described in WO 00/61537. Nitrate salts of drugs including pioglitazone are disclosed in WO 02/30867. Diazeniumdiolate derivatives have recently been recognized as alternatives for nitrates, setting free two molecules of NO under physiological conditions. A diazeniumdiolate derivative of tacrine is described by L. Fang et al., J. Med. Chem. 51, 7666-7669 (2008).

SUMMARY OF THE INVENTION

The invention relates to compounds of formula

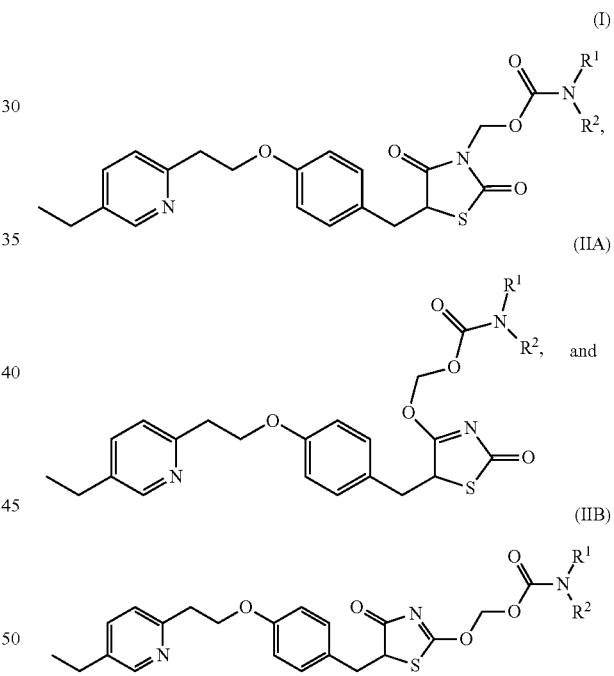

wherein
$R^1$ is $-(CH_2CH_2O)_aX$, $-(CH_2)_bOX$ or $-(CH_2)_cCH[(CH_2)_dOX]_2$;
$R^2$ is hydrogen, methyl, ethyl, $-(CH_2CH_2O)_aX$, $-(CH_2)_bOX$ or $-CH_2O(C=O)NH(CH_2CH_2O)_aX$;
X is $NO_2$ or $N=(NO)-R^3$;
$R^3$ is di($C_1$-$C_{18}$-alkyl)amino, di(2-aminoethyl)amino, N-2-aminoethyl-N-2-hydroxyethyl-amino, pyrrolidino, piperidino, piperazino, 4-($C_1$-$C_4$-alkyl)piperazino, 4-phenylpiperazino, 4-(2-pyridyl)piperazino or morpholino;
a is 1, 2 or 3;
b is between 1 and 6;
c is 1 or 2;
d is between 1 and 4;
and pharmaceutically acceptable salts thereof.

Furthermore the invention relates to pharmaceutical compositions comprising the compounds as defined hereinbefore, to the compounds as defined hereinbefore for the treatment of vascular and metabolic diseases, and to a method of treatment of vascular and metabolic diseases using the compounds and pharmaceutical compositions as defined hereinbefore.

The compounds of the invention represent combinations of useful medicaments for the treatment of patients with metabolic diseases, in particular of type 2 diabetes and its typical metabolic and vascular complications and/or concomitant diseases and disorders.

The compounds of the invention have superior vasodilating properties compared to pioglitazone.

DETAILED DESCRIPTION OF THE INVENTION

Figure 1:
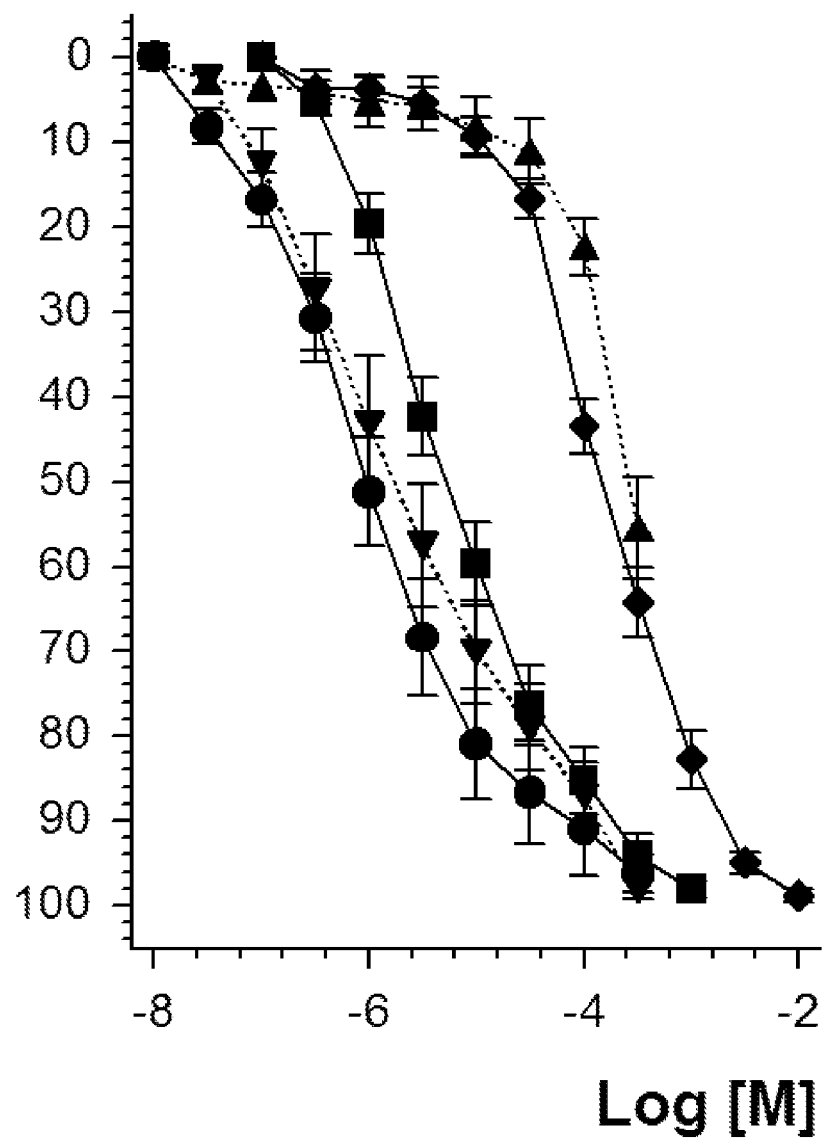
FIG. 1: Isometric tension.
Vasodilation of rat aortic ring segments preconstricted with phenylephrine, Example 2, Table 1. X-axis: relaxation in %; y-axis: log concentration (log M).
Very strong shift to the left from pioglitazone to pioglitazone nitrate 1, which is even more active than isosorbide dinitrate.
● Linker (chloromethyl N-2-nitrooxyethylcarbamate, 2), n=12
▲ Pioglitazone (PG), n=12
▼ Pioglitazone nitrate, compound 1, n=12
♦ Isosorbide-5-mononitrate (ISMN), n=20
■ Isosorbide dinitrate (ISDN), n=24
Figure 2:
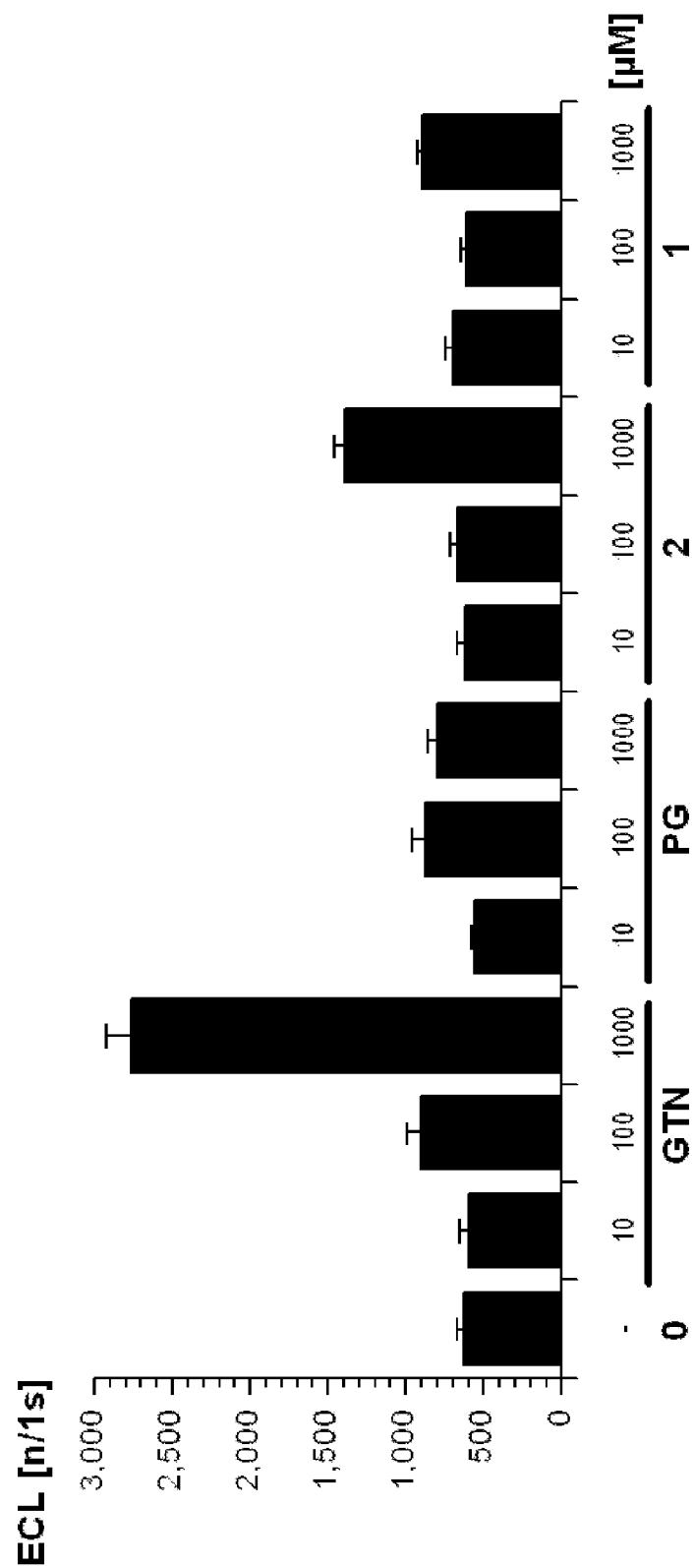
FIG. 2: ROS formation
Reactive oxygen and nitrogen species formation in response to in vitro challenge of isolated rat cardiac mitochondria based on reaction of the chemiluminescence dye L-012 (a luminal analogue), Example 3, Table 2. X-axis: compounds tested with concentration [μM]; y-axis: photons n per 1 sec of emission of chemiluminescence light (ECL). The ROS formation is the same for pioglitazone (PG) and pioglitazone nitrate 1, and substantially less than for glycerol trinitrate (GTN) and the linker (chloromethyl N-2-nitrooxyethylcarbamate, 2) at 1000 μM.
GTN: Glycerol trinitrate, 0: basal value (control).

The compound of formula (III) is 5-(4-[2-ethylpyridin-2-yl)ethoxy]benzyl)thiazolidine-2,4-dione, known under name of pioglitazone. Having a chiral carbon atom in the thiazolidinedione structure it may exist in two enantiomeric forms. Pioglitazone is the racemic mixture.

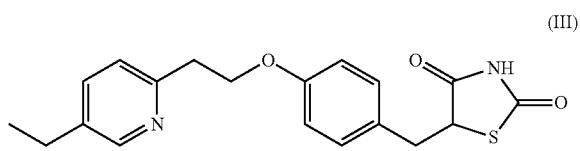 [SMILES: CCc1ccc(CCOc2ccc(CC3SC(=O)NC3=O)cc2)nc1]

(III)

The thiazolidinedione structure as shown in formula (III) is in equilibrium with its tautomeric enolimine isomers, wherein the proton shown attached to nitrogen in formula (III) is located on either one of the two oxygen atoms giving an enol and the double bond of the corresponding carbonyl group is shifted towards nitrogen resulting in an imine double bond.

It has now be found that the nitrated carbamate derivatives of formula (I) and the corresponding regioisomeric enolimine derivatives of formula (IIA) and (IIB) comprising one or two nitrate ester or diazeniumdiolate functions have advantageous properties. The invention relates to compounds of formula

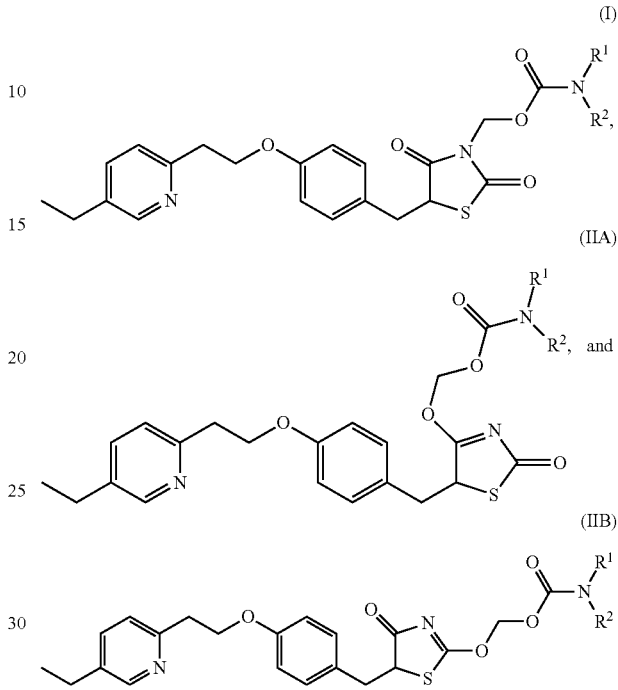

wherein
$R^1$ is $-(CH_2CH_2O)_aX$, $-(CH_2)_bOX$ or $-(CH_2)_cCH[(CH_2)_dOX]_2$;
$R^2$ is hydrogen, methyl, ethyl, $-(CH_2CH_2O)_aX$, $-(CH_2)_bOX$ or $-CH_2O(C=O)NH(CH_2CH_2O)_aX$;
X is $NO_2$ or $N=(NO)-R^3$;
$R^3$ is di($C_1$-$C_{18}$-alkyl)amino, di(2-aminoethyl)amino, N-2-aminoethyl-N-2-hydroxyethyl-amino, pyrrolidino, piperidino, piperazino, 4-($C_1$-$C_4$-alkyl)piperazino, 4-phenylpiperazino, 4-(2-pyridyl)piperazino or morpholino;
a is 1, 2 or 3;
b is between 1 and 6;
c is 1 or 2;
d is between 1 and 4;
and pharmaceutically acceptable salts thereof.

These compounds may be used to treat patients with metabolic diseases, in particular type 2 diabetes and its typical metabolic and vascular complications and/or concomitant diseases and disorders. Adding NO-donating properties on the molecular level to pioglitazone results in additional vasodilating properties as compared to pioglitazone which then results in improved glucose control and increased insulin sensitivity compared to the pioglitazone. These new additional properties are primarily the result of NO-mediated microvascular dilatation and corresponding increases in peripheral perfusion. Glucose control of type 2 diabetes patients is improved under chronic treatment, and HbA1 levels are significantly lowered. Other potential benefits include positive effects on lipid disorders and a reduction in cardiovascular risk.

$C_1$-$C_{18}$-alkyl is a linear or branched alkyl chain with up to 18 carbon atoms, for example n-octadecyl, n-hexadecyl, n-tetradecyl, n-octyl, isooctyl, n-heptyl, n-hexyl, n-pentyl, or $C_{1-4}$-alkyl, preferably n-hexyl or $C_{1-4}$-alkyl. In di($C_1$-$C_{18}$-alkyl)amino, the $C_1$-$C_{18}$-alkyl residues may be the same or different. For example, di($C_1$-$C_{18}$-alkyl)amino is dimethylamino, diethylamino, N-ethyl-N-methylamino, N-methyl-N-n-octadecylamino, N-n-hexadecyl-N-methylamino, or N-n-hexyl-N-methylamino.

$C_{1-4}$-alkyl is methyl, ethyl, n-propyl, isopropyl, n-butyl, isobutyl, sec-butyl, or tert-butyl, preferably methyl, ethyl or n-propyl, in particular methyl.

A pharmaceutically acceptable salt of a compound of formula (I), (IIA) or (IIB) is an organic or inorganic salt of a compound of the invention. Exemplary salts include, but are not limited to, acid addition salts, for example sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluene-sulfonate, and pamoate salts.

Compounds of formula (I), (IIA) and (IIB) can be manufactured by methods well known in the art. Preferably pioglitazone of formula (III) is treated with a carbamoylmethyl chloride, wherein the carbamate nitrogen is unsubstituted or substituted by a nitrate ester or diazeniumdiolate residue or a residue convertible to a nitrate ester or diazeniumdiolate, and optionally further substituted by methyl or ethyl. A residue convertible into a nitrate ester or a diazeniumdiolate is, e.g., a halide, in particular a bromide, connected to the carbamate nitrogen by way of an optionally branched alkylene group, an ethoxyethylene or an ethoxyethoxyethylene group. If the carbamate nitrogen is unsubstituted, a nitrate ester or diazeniumdiolate function is introduced e.g. by treatment with a linear alkylene dibromide, a branched alkylene tribromide, a bromoethoxyethyl bromide or a bromo-ethoxyethoxyethyl bromide, followed by replacement of the second (and optionally the third) bromo atom by a nitrate ester function through reaction with silver nitrate or by a diazeniumdiolate in a dipolar aprotic solvent. Alternatively, a bromoalkyl nitrate, branched bromoalkyl dinitrate, bromoethoxyethyl nitrate or bromoethoxyethoxyethyl nitrate may be used to alkylate the carbamate nitrogen. Likewise a diazeniumdiolate group may be introduced. Introduction of $R^1$ as a —$(CH_2CH_2O)_aX$ and $R^2$ as a —$CH_2O(C=O)NH(CH_2CH_2O)_aX$ group can be performed directly with the corresponding carbamoylmethyl chloride in excess, which alkylates the amide nitrogen atom of the thiazolidinedione and then also the carbamate nitrogen.

The enolimine parts of compounds of formula (IIA) and (IIB) represent tautomers of pioglitazone. Depending on the particular reaction conditions of the reaction with a carbamoylmethyl chloride, the carbamoylmethyl substituent not only attaches to the nitrogen atom in the amide tautomer of pioglitazone to give a compound of formula (I), but also to the enolimine oxygen atoms of the tautomers giving rise to regioisomeric carbamoylmethylated compounds of formula (IIA) and (IIB).

Preferred are compounds of formula (I), (IIA) and (IIB) wherein
$R^1$ is —$(CH_2CH_2O)_aX$, —$(CH_2)_bOX$ or —$(CH_2)_cCH[(CH_2)_dOX]_2$;
$R^2$ is hydrogen, —$(CH_2CH_2O)_aX$, —$(CH_2)_bOX$ or —$CH_2O(C=O)NH(CH_2CH_2O)_aX$;
X is $NO_2$ or N=(NO)—$R^3$;
$R^3$ is di($C_1$-$C_{18}$-alkyl)amino, di(2-aminoethyl)amino, N-2-aminoethyl-N-2-hydroxyethyl-amino, pyrrolidino, piperidino, piperazino, 4-($C_1$-$C_4$-alkyl)piperazino, 4-phenylpiperazino, 4-(2-pyridyl)piperazino or morpholino;
a is 1, 2 or 3;
b is between 1 and 6;
c is 1 or 2;
d is between 1 and 4;
and pharmaceutically acceptable salts thereof.

Further preferred are compounds of formula (I), (IIA) and (IIB) wherein
$R^1$ is —$(CH_2CH_2O)_aX$ or —$(CH_2)_bOX$;
$R^2$ is hydrogen, —$(CH_2CH_2O)_aX$, —$(CH_2)_bOX$ or —$CH_2O(C=O)NH(CH_2CH_2O)_aX$;
X is $NO_2$ or N=(NO)—$R^3$;
$R^3$ is diethylamino, di(2-aminoethyl)amino, N-2-aminoethyl-N-2-hydroxyethyl-amino, pyrrolidino, piperidino, piperazino, 4-methylpiperazino or morpholino;
a is 1, 2 or 3;
b is between 1 and 6;
and pharmaceutically acceptable salts thereof.

More preferred are compounds of formula (I), (IIA) and (IIB) wherein
$R^1$ is —$(CH_2CH_2O)_aX$ or —$(CH_2)_bOX$;
$R^2$ is hydrogen, —$(CH_2CH_2O)_aX$, —$(CH_2)_bOX$ or —$CH_2O(C=O)NH(CH_2CH_2O)_aX$;
X is $NO_2$ or N=(NO)—$R^3$;
$R^3$ is diethylamino or pyrrolidino;
a is 1 or 2;
b is 2, 3 or 4;
and pharmaceutically acceptable salts thereof.

Further preferred are compounds of formula (I), (IIA) and (IIB) wherein
$R^1$ is —$CH_2CH_2ONO_2$; and
$R^2$ is hydrogen, —$CH_2CH_2ONO_2$ or —$(CH_2O(C=O)NHCH_2CH_2ONO_2$; and pharmaceutical acceptable salts thereof.

Even more preferred are compounds of formula (I) wherein
$R^1$ is —$CH_2CH_2ONO_2$; and
$R^2$ is hydrogen or —$CH_2CH_2ONO_2$.

Most preferred are the compounds of the Examples.

The present invention relates also to pharmaceutical compositions that comprise a compound of formula (I), (IIA) and (IIB) as active ingredient and that can be used especially in the treatment of the diseases mentioned above. Compositions for enteral administration, such as nasal, buccal, rectal or, especially, oral administration, and for parenteral administration, such as intravenous, intramuscular or subcutaneous administration, to warm-blooded animals, especially humans, are especially preferred. The compositions comprise the active ingredient alone or, preferably, together with a pharmaceutically acceptable carrier. The dosage of the active ingredient depends upon the disease to be treated and upon the species, its age, weight, and individual condition, the individual pharmacokinetic data, and the mode of administration.

The present invention relates especially to pharmaceutical compositions that comprise a compound of formula (I), (IIA) and (IIB) or a pharmaceutically acceptable salt of a compound of formula (I), (IIA) and (IIB), and at least one pharmaceutically acceptable carrier.

The invention relates also to pharmaceutical compositions for use in a method for the prophylactic or especially therapeutic management of the human or animal body, in particular in a method of treating a metabolic disease, especially those mentioned above.

The invention relates also to processes and to the use of compounds of formula (I), (IIA) and (IIB) for the preparation of pharmaceutical preparations which comprise compounds of formula (I), (IIA) and (IIB) as active component (active ingredient).

A pharmaceutical composition for the prophylactic or especially therapeutic management of a metabolic disease, of a warm-blooded animal, especially a human, comprising a novel compound of formula (I), (IIA) or (IIB) as active ingredient in a quantity that is prophylactically or especially therapeutically active against the said diseases, is likewise preferred.

The pharmaceutical compositions comprise from approximately 1% to approximately 95% active ingredient, single-dose administration forms comprising in the preferred embodiment from approximately 20% to approximately 90% active ingredient and forms that are not of single-dose type comprising in the preferred embodiment from approximately 5% to approximately 20% active ingredient. Unit dose forms are, for example, coated and uncoated tablets, ampoules, vials, suppositories, or capsules. Further dosage forms are, for example, ointments, creams, pastes, foams, tinctures, lipsticks, drops, sprays, dispersions, etc. Examples are capsules containing from about 0.01 g to about 1.0 g active ingredient.

The pharmaceutical compositions of the present invention are prepared in a manner known per se, for example by means of conventional mixing, granulating, coating, dissolving or lyophilizing processes.

Preference is given to the use of solutions of the active ingredient, and also suspensions or dispersions, especially isotonic aqueous solutions, dispersions or suspensions which, for example in the case of lyophilized compositions comprising the active ingredient alone or together with a carrier, for example mannitol, can be made up before use. The pharmaceutical compositions may be sterilized and/or may comprise excipients, for example preservatives, stabilizers, wetting agents and/or emulsifiers, solubilizers, salts for regulating osmotic pressure and/or buffers and are prepared in a manner known per se, for example by means of conventional dissolving and lyophilizing processes. The said solutions or suspensions may comprise viscosity-increasing agents, typically sodium carboxymethylcellulose, carboxymethylcellulose, dextran, polyvinylpyrrolidone, or gelatins, or also solubilizers, e.g. Tween 80® (polyoxyethylene(20)sorbitan mono-oleate).

Suspensions in oil comprise as the oil component the vegetable, synthetic, or semi-synthetic oils customary for injection purposes. In respect of such, special mention may be made of liquid fatty acid esters that contain as the acid component a long-chained fatty acid having from 8 to 22, especially from 12 to 22, carbon atoms. The alcohol component of these fatty acid esters has a maximum of 6 carbon atoms and is a monovalent or polyvalent, for example a mono-, di- or trivalent, alcohol, especially glycol and glycerol. As mixtures of fatty acid esters, vegetable oils such as cottonseed oil, almond oil, olive oil, castor oil, sesame oil, soybean oil and groundnut oil are especially useful.

The manufacture of injectable preparations is usually carried out under sterile conditions, as is the filling, for example, into ampoules or vials, and the sealing of the containers.

Suitable carriers are especially fillers, such as sugars, for example lactose, saccharose, mannitol or sorbitol, cellulose preparations, and/or calcium phosphates, for example tricalcium phosphate or calcium hydrogen phosphate, and also binders, such as starches, for example corn, wheat, rice or potato starch, methylcellulose, hydroxypropyl methyl-cellulose, sodium carboxymethylcellulose, and/or polyvinylpyrrolidone, and/or, if desired, disintegrators, such as the above-mentioned starches, also carboxymethyl starch, crosslinked polyvinylpyrrolidone, alginic acid or a salt thereof, such as sodium alginate. Additional excipients are especially flow conditioners and lubricants, for example silicic acid, talc, stearic acid or salts thereof, such as magnesium or calcium stearate, and/or polyethylene glycol, or derivatives thereof.

Tablet cores can be provided with suitable, optionally enteric, coatings through the use of, inter alia, concentrated sugar solutions which may comprise gum arabic, talc, polyvinyl-pyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropyl-methylcellulose phthalate. Dyes or pigments may be added to the tablets or tablet coatings, for example for identification purposes or to indicate different doses of active ingredient.

Pharmaceutical compositions for oral administration also include hard capsules consisting of gelatin, and also soft, sealed capsules consisting of gelatin and a plasticizer, such as glycerol or sorbitol. The hard capsules may contain the active ingredient in the form of granules, for example in admixture with fillers, such as corn starch, binders, and/or glidants, such as talc or magnesium stearate, and optionally stabilizers. In soft capsules, the active ingredient is preferably dissolved or suspended in suitable liquid excipients, such as fatty oils, paraffin oil or liquid polyethylene glycols or fatty acid esters of ethylene or propylene glycol, to which stabilizers and detergents, for example of the polyoxy-ethylene sorbitan fatty acid ester type, may also be added.

Pharmaceutical compositions suitable for rectal administration are, for example, suppositories that consist of a combination of the active ingredient and a suppository base. Suitable suppository bases are, for example, natural or synthetic triglycerides, paraffin hydrocarbons, polyethylene glycols or higher alkanols.

For parenteral administration, aqueous solutions of an active ingredient in water-soluble form, for example of a water-soluble salt, or aqueous injection suspensions that contain viscosity-increasing substances, for example sodium carboxymethylcellulose, sorbitol and/or dextran, and, if desired, stabilizers, are especially suitable. The active ingredient, optionally together with excipients, can also be in the form of a lyophilizate and can be made into a solution before parenteral administration by the addition of suitable solvents.

Solutions such as are used, for example, for parenteral administration can also be employed as infusion solutions.

Preferred preservatives are, for example, antioxidants, such as ascorbic acid, or microbicides, such as sorbic acid or benzoic acid.

The present invention relates furthermore to a method for the treatment of a metabolic disease, which comprises administering a compound of formula (I), (IIA) or (IIB), or a pharmaceutically acceptable salt thereof, wherein the radicals and symbols have the meanings as defined above for formula (I), in a quantity effective against said disease, to a warm-blooded animal requiring such treatment. The compounds of formula (I), (IIA) and (IIB) can be administered as such or especially in the form of pharmaceutical compositions, prophylactically or therapeutically, preferably in an amount effective against the said diseases, to a warm-blooded animal, for example a human, requiring such treatment. In the case of an individual having a bodyweight of about 70 kg the daily dose administered is from approximately 0.01 g to approximately 5 g, preferably from approximately 0.25 g to approximately 1.5 g, of a compound of the present invention.

The present invention relates especially also to the use of a compound of formula (I), (IIA) or (IIB), or a pharmaceutically acceptable salt thereof, as such or in the form of a pharmaceutical formulation with at least one pharmaceutically acceptable carrier for the therapeutic and also prophylactic management of vascular and metabolic diseases, in particular of type 2 diabetes and its typical metabolic and vascular complications and/or concomitant diseases and disorders.

Examples of typical metabolic complications and disorders considered here are impaired glucose tolerance (including pre-diabetic stages) and decreased insulin sensitivity, and specifically all disorders of lipid metabolism such as dyslipidaemias, specifically hypercholesterolaemia, hypertriglyceridaemia, abnormalities of high density lipoproteins alone or in combinations with other dyslipidaemias, abnormalities of Apolipoprotein A1 or other subfractions of lipoproteins, and other metabolic diseases associated with, or including type 2 diabetes or decreased glucose tolerance such as metabolic syndrome and the associated vascular and metabolic complications leading to an increased cardiovascular risk in these patients.

Examples for typical vascular complications and diseases in type 2 diabetic patients are hypertension and atherosclerosis and related consecutive diseases and complications, in particular, those attributed to microvascular disease such as cerebral ischaemia in general and, specifically, transient ischaemic attacks (TIAs), prolonged neurological deficits (PRIND), stroke (ischaemic and non-ischaemic), chronic cerebrovascular diseases, coronary artery disease and its various manifestations, peripheral arterial disease (PAD) at all stages, specifically including abnormalities in micro- and macrovascular function such as neuropathy, endothelial dysfunction, cold feet, impaired wound healing, ischaemic ulcers and necrosis, critical limb ischaemia, and intermittent claudication.

The following Example serves to illustrate the invention without limiting the invention in its scope.

Example 1

(2-Nitroxyethyl)carbamic acid 5-(4-[2-ethylpyridin-2-yl)ethoxy]benzyl)-2,4-dioxothiazolidin-3-ylmethyl ester (1)

ethyl acetate:heptane) to give the title compound (5-(4-(2-(5-ethylpyridin-2-yl)ethoxy)benzyl)-2,4-dioxothiazolidin-3-yl) methyl 2-(nitrooxy)ethylcarbamate (1), 5.3 g (30%), as a white solid.

$^1$H NMR: δ 8.41 (s, 1H), 7.50 (d, J=7, 1H), 7.21 (d, J=7, 1H), 7.15 (d, J=7, 2H), 6.82 (d, J=7, 2H), 5.50 (q, J=9, 2H), 5.40 (br s, 1H), 4.58 (t, J=2, 2H), 4.45 (dd, J=7, 2, 1H), 4.35 (t, J=7, 2H), 3.55 (q, J=3, 2H), 3.45 (dd, J=12, 2, 1H), 3.25 (t, J=7, 2H), 3.10 (dd, J=12, 7, 1H), 2.68 (q, J=7.5, 2H), 1.30 (t, J=7.5, 3H). $^{13}$C NMR: δ 172.6, 170.0, 158.4, 155.5, 154.4, 148.8, 137.3, 136.1, 130.4, 127.3, 123.4, 114.9, 71.5, 67.3, 63.6, 51.8, 38.5, 37.6, 37.4, 25.7, 15.3. LCMS: 519 (M+H$^+$), 443.

The starting material chloromethyl N-2-nitrooxyethylcarbamate (2) is obtained as follows:

20 g Ethanolamine (328 mmol) is added dropwise to 60 g HNO$_3$ (100%) at −20° C., care being taken that the temperature does not rise above 5° C. The mixture is added to ethyl ether (300 g) and stirred for 1 h at 0° C. The obtained suspension is filtered, the solids washed with ethyl ether and dissolved in ethanol (120 g) at 30° C. On cooling to 0° C., the product precipitates again. The solids are added in portions to 60 g HNO$_3$ (100%) at −5° C., then cooled to −15° C., and treated with ethanol. Ethyl ether (200 g) is added, and the mixture stirred 1 h at −10° C. The obtained suspension is filtered, the solids washed with ethyl ether, and dried in hot air to give 21.9 g (41%) white crystals of 2-nitroxyethyl-ammonium nitrate.

4.25 g Chloromethyl chloroformate (33.0 mmol) are added dropwise in 15 min to 5.0 g 2-nitroxyethylammonium nitrate (29.6 mmol) and 7.5 g triethylamine (74.1 mmol) in 130 g CH$_2$Cl$_2$ at −15° C. The mixture is stirred at −10° C. for 1 h. Water (40 g) is added, the organic phase washed with aqueous citric acid (10%) and saturated aqueous NaHCO$_3$, then dried

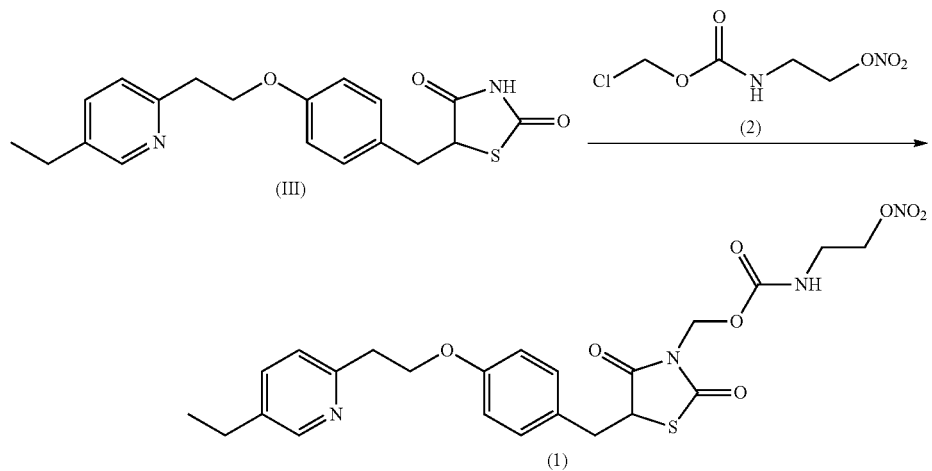

A solution of chloromethyl 2-(nitrooxy)ethylcarbamate (2, 13.37 g, 67.3 mmol) in CH$_2$Cl$_2$ (20 ml) is added drop-wise to a suspension of 5-(4-(2-(5-ethylpyridin-2-yl)ethoxy)benzyl)-thiazolidine-2,4-dione (pioglitazone, 12 g, 33.7 mmol) in CH$_2$Cl$_2$ (160 ml) and triethylamine (9.38 ml, 67.3 mmol) at 22° C. (room temperature) under an argon atmosphere. The reaction is stirred for 8 h. The reaction is diluted with CH$_2$Cl$_2$ and H$_2$O and the layers separated. The organic layer is dried (MgSO$_4$) and the solvent evaporated to give the crude product. The crude material is purified by column chromatography (silica, 40:60 ethyl acetate:heptane, product R$_f$ 0.3 (80:20 over Na$_2$SO$_4$, and evaporated to give 4.6 g (78%) of a yellowish oil. $^1$H-NMR (200 MHz, CDCl$_3$): 3.53-3.63 (m, 2H); 4.57 (t, J=5.1, 2 H); 5.74 (s, 2H).

Example 2

Vasodilatory Potency of Pioglitazone Nitrate (1)

For in vitro characterization of the new pioglitazone nitrate (1) of Example 1, vasodilatory potency was determined by isometric tension studies. According to a published procedure rat aortic ring segments were preconstricted by the alpha-receptor-agonist phenylephrine [Daiber, A. et al., Mol Pharmacol 66 (2004), 1372-1382; Wendt, M. et al., Free Radic Biol Med 39 (2005), 381-391; Munzel, T. et al., J Clin Invest 95 (1995), 187-194]. After reaching a stable preconstriction of vascular tone, the vessels were dose-dependently vasodilated until the final tone at the highest added concentration of the vasodilator was reached. The vasodilators were added at half-logarithmic concentrations starting at $10^{-8}$ M (=10 nanomolar). Vasodilatory potency was compared creating a concentration-relaxation curve. The data are based on experiments with aorta from at least 6 rats on 3 different days. Pioglitazone nitrate 1 was more potent ($pD_2$-value approximately 6) than isosorbide dinitrate (ISDN) ($pD_2$-value approximately 5.5). The linker chloromethyl N-2-nitrooxy-ethyl-carbamate (2) showed a similar strong vasodilatory potency ($pD_2$-values approximately 6). The parent structure pioglitazone showed weak relaxing effects itself ($pD_2$-value approximately 3.5).

TABLE 1

Isometric tension
(Mean ± SEM)

| Log [M] | Linker 2 n = 12 | Pioglitazone n = 12 | 1 n = 12 | ISMN n = 20 | ISDN n = 8 |
|---|---|---|---|---|---|
| −8 | 0 | 0 | 0 | | |
| −7.5 | 8.25 ± 2.09 | 2.92 ± 1.49 | 2.65 ± 1.49 | | |
| −7 | 16.85 ± 3.29 | 3.42 ± 1.68 | 12.82 ± 1.68 | 0 | 0 |
| −6.5 | 30.73 ± 5.12 | 4.14 ± 2.57 | 27.72 ± 2.57 | 3.86 ± 1.04 | 5.49 ± 1.42 |
| −6 | 51.19 ± 6.35 | 5.40 ± 2.88 | 43.34 ± 2.88 | 3.73 ± 1.39 | 19.70 ± 3.46 |
| −5.5 | 68.37 ± 6.89 | 5.63 ± 3.15 | 57.49 ± 3.15 | 5.47 ± 1.95 | 42.34 ± 4.62 |
| −5 | 80.97 ± 6.47 | 8.30 ± 3.49 | 70.11 ± 3.49 | 9.29 ± 2.23 | 59.64 ± 4.97 |
| −4.5 | 86.66 ± 6.04 | 11.19 ± 3.82 | 79.07 ± 3.82 | 16.76 ± 2.29 | 76.54 ± 4.69 |
| −4 | 91.00 ± 5.36 | 22.40 ± 3.34 | 87.22 ± 3.34 | 43.46 ± 3.28 | 85.32 ± 3.92 |
| −3.5 | 96.18 ± 2.20 | 55.47 ± 5.98 | 98.13 ± 5.98 | 64.17 ± 4.11 | 94.10 ± 2.50 |
| −3 | | | | 82.81 ± 3.45 | 98.04 ± 1.02 |
| −2.5 | | | | 94.91 ± 1.28 | |
| −2 | | | | 98.77 ± 0.75 | |

ISMN: Isosorbide-5-mononitrate
ISDN: Isosorbide dinitrate

Example 3

Lack of Vascular Oxidative Stress Caused by Pioqlitazone Nitrate (1)

Vascular oxidative stress is a well-known side effect of nitrate tolerance (an adverse condition that develops under chronic nitrate therapy). Therefore, the induction of reactive oxygen and nitrogen species formation in response to in vitro challenges with the test compounds was assessed in isolated mitochondria according to a published procedure [Daiber, A. et al., Mol Pharmacol 66 (2004), 1372-1382; Daiber, A. et al., Biochem Biophys Res Commun 338 (2005), 1865-1874; Daiber, A. et al., Mol Pharmacol 68 (2005), 579-588]. The assay is based on the reaction of the chemiluminescence dye L-012 (a luminol analogue) with reactive oxygen and nitrogen species (RONS, e.g. superoxide anion radicals, peroxynitrite anions or nitrogen dioxide radicals) and subsequent emission of chemiluminescence light (ECL). The signal is counted in photons/time (=counts/30s). The data are based on experiments with cardiac mitochondria from at least 6 rats on 3 different days. The results demonstrate that glycerol trinitrate (GTN) increases the RONS signal in a concentration-dependent fashion. The linker chloromethyl N-2-nitrooxy-ethyl-carbamate (2) has also some increasing effect. Pioglitazone nitrate 1 is comparable to pioglitazone and does not have a pronounced effect on RONS formation.

TABLE 2

| | ROS formation (counts/1 s) | | | |
|---|---|---|---|---|
| Compound | Conc. | Mean | SEM | n |
| Basal | — | 627.7 | 41.2 | 6 |
| Glycerol trinitrate | 10 μM | 597.7 | 60.4 | 6 |
| | 100 μM | 898.5 | 95.3 | 6 |
| | 1000 μM | 2762 | 164.9 | 6 |
| Pioglitazone | 10 μM | 563 | 15.6 | 6 |
| | 100 μM | 874.5 | 84.9 | 8 |
| | 1000 μM | 801.7 | 61.0 | 6 |
| Linker chloromethyl N-2-nitrooxyethylcarbamate, 2 | 10 μM | 622.5 | 52.3 | 6 |
| | 100 μM | 674.7 | 37.5 | 6 |
| | 1000 μM | 1395.8 | 64.1 | 6 |
| Pioglitazone nitrate 1 | 10 μM | 697.3 | 48.2 | 6 |
| | 100 μM | 609.8 | 38.2 | 6 |
| | 1000 μM | 889.2 | 41.1 | 6 |

The invention claimed is:
1. A compound of formula

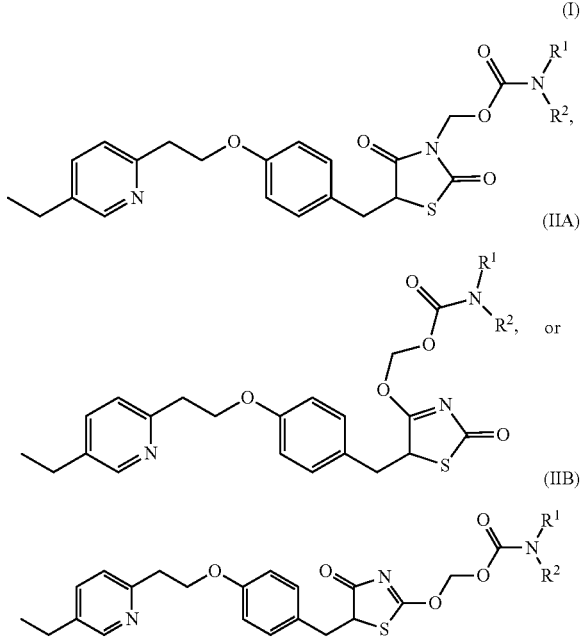

wherein
R¹ is —(CH₂CH₂O)ₐX, —(CH₂)ᵦOX or —(CH₂)꜀CH[(CH₂)ₔOX]₂;
R² is hydrogen, methyl, ethyl, —(CH₂CH₂O)ₐX, —(CH₂)ᵦOX or —CH₂O(C=O)NH(CH₂CH₂O)ₐX;
X is NO₂ or N=(NO)—R³;
R³ is di(C₁-C₁₈-alkyl)amino, di(2-aminoethyl)amino, N-2-aminoethyl-N-2-hydroxyethyl-amino, pyrrolidino, piperidino, piperazino, 4-(C₁-C₄-alkyl)piperazino, 4-phenylpiperazino, 4-(2-pyridyl)piperazino or morpholino;
a is 1, 2 or 3;
b is between 1 and 6;
c is 1 or 2;
d is between 1 and 4;
and pharmaceutically acceptable salts thereof.

2. The compound of formula (I), (IIA) or (IIB) according to claim 1 wherein
R¹ is —(CH₂CH₂O)ₐX, —(CH₂)ᵦOX or —(CH₂)꜀CH[(CH₂)ₔOX]₂;
R² is hydrogen, —(CH₂CH₂O)ₐX, —(CH₂)ᵦOX or —CH₂O(C=O)NH(CH₂CH₂O)ₐX;
X is NO₂ or N=(NO)—R³;
R³ is di(C₁-C₁₈-alkyl)amino, di(2-aminoethyl)amino, N-2-aminoethyl-N-2-hydroxyethyl-amino, pyrrolidino, piperidino, piperazino, 4-(C₁-C₄-alkyl)piperazino, 4-phenylpiperazino, 4-(2-pyridyl)piperazino or morpholino;
a is 1, 2 or 3;
b is between 1 and 6;
c is 1 or 2;
d is between 1 and 4;
and pharmaceutically acceptable salts thereof.

3. The compound of formula (I), (IIA) or (IIB) according to claim 1 wherein
R¹ is —(CH₂CH₂O)ₐX or —(CH₂)ᵦOX;
R² is hydrogen, —(CH₂CH₂O)ₐX, —(CH₂)ᵦOX or —CH₂O(C=O)NH(CH₂CH₂O)ₐX;
X is NO₂ or N=(NO)—R³;
R³ is diethylamino, di(2-aminoethyl)amino, N-2-aminoethyl-N-2-hydroxyethyl-amino, pyrrolidino, piperidino, piperazino, 4-methylpiperazino or morpholino;
a is 1, 2 or 3;
b is between 1 and 6;
and pharmaceutically acceptable salts thereof.

4. The compound of formula (I), (IIA) or (IIB) according to claim 1 wherein
R¹ is —(CH₂CH₂O)ₐX or —(CH₂)ᵦOX;
R² is hydrogen, —(CH₂CH₂O)ₐX, —(CH₂)ᵦOX or —CH₂O(C=O)NH(CH₂CH₂O)ₐX;
X is NO₂ or N=(NO)—R³;
R³ is diethylamino or pyrrolidino;
a is 1 or 2;
b is 2, 3 or 4;
and pharmaceutically acceptable salts thereof.

5. The compound of formula (I), (IIA) or (IIB) according to claim 1 wherein
R¹ is —CH₂CH₂ONO₂; and
R² is hydrogen, —CH₂CH₂ONO₂ or —CH₂O(C=O)NHCH₂CH₂ONO₂; and
pharmaceutical acceptable salts thereof.

6. The compound of formula (I) according to claim 1 wherein
R¹ is —CH₂CH₂ONO₂; and
R² is hydrogen or —CH₂CH₂ONO₂.

7. (2-Nitrooxyethyl)carbamic acid 5-(4-[2-ethylpyridin-2-yl)ethoxy]benzyl)-2,4-dioxothiazolidin-3-ylmethyl ester according to claim 1.

8. A pharmaceutical composition comprising a compound of formula (I), (IIA) or (IIB), or a pharmaceutically acceptable salt thereof according to claim 1 and at least one pharmaceutically acceptable carrier.

9. A method for the treatment of type 2 diabetes, which comprises administering a compound of formula (I), (IIA) or (IIB), or a pharmaceutically acceptable salt thereof according to claim 1 in an effective amount, to a warm-blooded animal requiring the treatment.

* * * * *